United States Patent [19]

Kwoh

[11] Patent Number: 5,078,140
[45] Date of Patent: Jan. 7, 1992

[54] IMAGING DEVICE - AIDED ROBOTIC STEREOTAXIS SYSTEM

[76] Inventor: Yik S. Kwoh, 2801 Atlantic Ave., Long Beach, Calif. 90801

[21] Appl. No.: 910,527

[22] Filed: Sep. 23, 1986

Related U.S. Application Data

[63] Continuation-in-part of Ser. No. 860,840, May 8, 1986, abandoned.

[51] Int. Cl.$^5$ ............................................. A61B 6/00
[52] U.S. Cl. ................................. 128/653.1; 606/130; 378/20; 901/6; 901/16; 901/41
[58] Field of Search .................... 128/303 B, 653, 660; 378/20, 205; 364/414, 513; 901/6, 9, 16, 41

[56] References Cited

U.S. PATENT DOCUMENTS

| | | | |
|---|---|---|---|
| 3,720,817 | 3/1973 | Dinwiddie | 364/414 |
| 3,735,755 | 5/1973 | Eggleton et al. | 128/24 A |
| 4,118,631 | 10/1978 | Froggart | 378/20 |
| 4,436,684 | 3/1984 | White | 128/653 |
| 4,580,561 | 4/1986 | Williamson | 128/303 B |
| 4,581,566 | 4/1986 | Ekstrom et al. | 364/513 |
| 4,583,538 | 4/1986 | Onik et al. | 128/303 B |
| 4,598,368 | 7/1986 | Umemura | 364/414 |
| 4,617,925 | 10/1986 | Laitinen | 128/303 B |

OTHER PUBLICATIONS

Computer Graphics and an Interactive Stereotactic System for CT-Aided Neurosurgery, Michael L. Rhodes, IEEE Computer Graphics and Applications, Computer Graphics in Medicine & Biology, Aug. 1983, pp. 31-37.
Stereotactic Neurosurgery Using 3-D Image Data From Computed Tomography, Michael L. Rhodes, Ph.D., Journal of Medical Systems, vol. 6, No. 1, 1982, pp. 106-118.
Improving the Absolute Positioning Accuracy of Robot Manipulators, S. Hayati & M. Mirmirani, Journal of Robotic Systems, 2(4), (1986), pp. 397-413.
Guided Brain Operations, Methodological and Clinical Developments in Stereotactic Surgery, Ernest A. Spiegel, Karger, Contributions to the Physiology of Subcortical Structures, pp. 24-34.
An Improved CT-Aided Stererotactic Neurosurgery Technique, IEEE reprinted from Proceedings of the Fifth Annual Symposium on Computer Applications in Medical Care, Nov. 1981 (1981), pp. 591-595.
CT-Guided Stereotactic Biopsies Using a Modified Frame and Gildenberg Techniques, Dennis E. Bullard, Journal of Neurology, Neurosurgery and Psychiatry 1984, pp. 590-595.
Stereotactic Exploration of the Brain the Era of Computed Tomography, L. Dade Lunsford, M.D., Surg. Neurol, 1984, pp. 222-230.
Preliminary Experience with Brown-Robert-Wells (BRW) Computerized Tomography Stereotaxis Guidance System, M. Peter Heilburn, M.D., J. Neurosurgery, vol. 59, Aug. 1983, pp. 217-221.
A New Computerized Tomographic-Aided Robotic Stereotaxis System, Y. S. Kwoh, Ph.D., Robotics Age, Jun. 1985, pp. 17-20.

*Primary Examiner*—Ruth S. Smith
*Attorney, Agent, or Firm*—Lyon & Lyon

[57] ABSTRACT

An apparatus and method for computer controlled stereotactic surgery is disclosed. This method utilizes an imaging device, a robotic arm and a means for controlling the robotic arm. Stereotactic surgery on integral body parts, e.g. the brain, spine, knee or other joint, breast, etc. may be accomplished with relatively greater precision and smaller incisions. The imaging device, which may be a computerized tomography (CT) axial imaging system, a magnetic resonance imaging (MRI) device, or any suitable image-providing means, provides information regarding the structure of the bodily location to be operated on. The robotic arm is utilized to precisely orient the surgical tools or other implements used in conducting the surgery or related procedure. The control means, such as a computer, utilizes information received from the imaging device, alone or together with other information, to control the robotic arm.

14 Claims, 3 Drawing Sheets

IMAGING DEVICE - AIDED ROBOTIC STEREOTAXIS SYSTEM

This application is a continuation-in-part of my copending application Ser. No. 860,840, filed May 8, 1986 now abandoned.

BACKGROUND OF THE INVENTION

Field of the Invention

Stereotaxis is a technique that has been developed and used for almost 80 years since Horsley and Clarke first invented the 3-D stereotactic machine; see Horsley et al, "On the Intrinsic Fibres of the Cerebellum, Its Nuclei and Its Efferent Tracts", *Brain*, 28, pp. 12-29 (1905); Horsley et al, "The Structure and Functions of the Cerebellum Examined by a New Method", *Brain*, 31, p. 45 (1908). Since this pioneering effort, many types of stereotactic equipment have been devised; see for example, Ingram et al, "Results of Stimulation of the Tegmentum with the Horsley-Clarke Stereotaxis Apparatus", *Arch. Neurol. Psyciatrt.*, 28, 512-541 (1932); Leksell, "The Stereotactic Method and Radiosurgery of the Brain", *Acta Chir. Scand.*, 102, 315-319 (1951); Barcia-Salorio et al, "Tomography in Stereotaxis: A New Stereoencephalotome Designed for this Purpose", *Acta Neurochir. Suppl.*, 24, 77-83 (1977). In the early practice of stereotactic surgery the road map to the target was provided by conventional x-ray pictures that were often enhanced by contrast material techniques.

In the late 1970s, the integration of stereotaxis with computerized tomographic (CT) scanning provided a much more powerful tool for surgeons. This technique used high-resolution axial two-dimensional pictures to guide the probe to the target accurately. Several groups have developed CT-aided stereotactic head frames for intracranial operations; see Brown, "A Computerized Tomography-Computer Graphics Approach to Stereotactic Localization", *Journal of Neurosurgery*, 50, 715-720 (June 1979); Brown, "A Stereotactic Head Frame for Use with CT Body Scanners", *Investigative Radiology*, 14, 300-304 (July-August 1979); Brown et al, "Stereotactic Frame and Computer Software for CT-Directed Neurosurgical Locations", *Investigative Radiology*, 15, 308-312 (July-August 1980); Second Annual Symposium on Parkinson's Disease, *Journal of Neurosurgery*, 24, 430-481 (1966); Shao et al, "A New CT-Aided Stereotactic Neurosurgery Technique", to be published in *IEEE Trans. on Biomedical Engineering*. The brain is ideally suited for such procedures because of the availability of rigid skull fixation and the absence of physiologic motion.

Recently, a CT-aided stereotactic body frame was announced by Siemens. An independent parallel effort in this direction has also been tested; Lightfoot et al, "A Computer Assisted Stereotactic Procedure System for CT Scanners"; submitted to *IEEE Trans. on Biomedical Engineering*. These approaches extended precision stereotaxis to the whole human body.

Stereotactic neurosurgery is a technique for guiding the tip of a probe or other delicate instrument to a predetermined point in the nervous system without direct viewing of the surgical site. Referencing is provided by a stereotactic landmark, for example a head frame or brace into which the patient's head is placed. Reference marks along two axes are used to locate and position surgical instruments. To visualize the interior of the skull, a CT scan is used, providing two-dimentional, high-resolution, axial pictures that show detailed soft-tissued anatomy inside the cranial vault and the spinal cord.

Until now, all previous stereotactic techniques, not just those used in neurosurgery, involved the use of some type of stereotactic "frame." However, the use of a frame presents the surgeon with several problems. The manual reading, setting and adjustment of the frame parameters is a time-consuming process, error prone when frequent maneuvers are required, and thus makes frequent trajectory modifications difficult. A motorized frame could help solve this problem, but such a system tends to be heavy and bulky. A frame is usually designed only for the head or body. Although a frame intended for application to both the head and body has been designed, see the Lightfoot et al article mentioned above, to date its performance has not been satisfactory.

The fixed radius of a frame arch also lacks the flexibility that surgeons prefer. For example, the surgeon often wishes to place the probe holder as close to the patient as possible, which requires a small arch. But if one builds a frame with the required small arch, it cannot be used with an oversized patient. Further, each frame, depending on its structure and design, has unreachable corners. On occasion, the desired trajectory is within one of these forbidden zones of the frame. In prior frames of this type, the physical difficulties of reading the CT scan data and setting appropriate parameters on the frame could lead to human errors. Finally, such frame structures hamper the surgeon's view of the patient, making some surgical procedures quite difficult, and a frame between surgeon and patient can in general be an awkward arrangement.

There is thus a need to replace hitherto-employed stereotactic frames with other means which will permit more widespread and convenient use of stereotactic surgery in a greater variety of procedures useable on larger numbers of human and veterinary patients.

Accordingly it is an object of this invention to provide a novel apparatus and method for conducting stereotactic surgery.

It is also an object of this invention to provide a novel apparatus and method for conducting stereotactic surgery and related procedures of all types which dispense with the need for a stereotactic frame.

A further object of this invention is to provide a novel apparatus and method for conducting stereotactic surgery and related procedures of all types which provide the surgeon with a flexible, speedy and accurate means of conducting such procedures, thus permitting increasingly sophisticated stereotactic procedures to be conducted.

These and other objects, as well as the nature, scope and utilization of the invention, will become readily apparent to those skilled in the art from the following description, the drawings, and the appended claims.

SUMMARY OF THE INVENTION

The novel apparatus of this invention includes:

an imaging device, which may be a computerized tomography (CT) imaging system, a magnetic resonance imaging (MRI) device, a positron emission tomography (PET) imaging device, an ultrasound device, a mammograph machine, or any other device for obtaining internal images of the body, or combinations of such devices, e.g., a CT image overlaid with an MRI image, to provide information regarding the structure of the bodily location—the brain, spine, knee or other joint, breast, etc.—to be operated on;

a robotic arm to precisely orient the surgical tools or other implements used in conducting the surgery or related procedure, and control means, such as a computer, for controlling the robotic arm based at least in part upon the information obtained from the imaging device.

Examples of the novel method of this invention, i.e., practicing computer controlled stereotactic surgery using the above-described novel apparatus, are given hereinbelow.

DETAILED DESCRIPTION OF THE INVENTION

Considering first the robotic arm element of the apparatus of this invention, a robotic arm suitable for stereotactic purposes must have several properties. First, it must have substantial maneuvering capability. Ideally, stereotactic surgery requires the surgeon to have complete access to position the robotic arm and its probe. In addition, the robotic arm must have an appropriate reach in order to provide an unobstructing support of the probe over the entire area. It must be sturdy enough to provide very stable probe trajectory, and should have sufficient fail-safe features to prevent it from causing damage should it malfunction. The robot system and its backup systems must also be highly reliable to avoid breakdowns during surgery. The size and the weight of the robotic arm should be such that the arm is as small and portable as possible. The robotic arm is itself a surgical tool that the surgeon should be able to move about quickly during an emergency.

Figure 1:
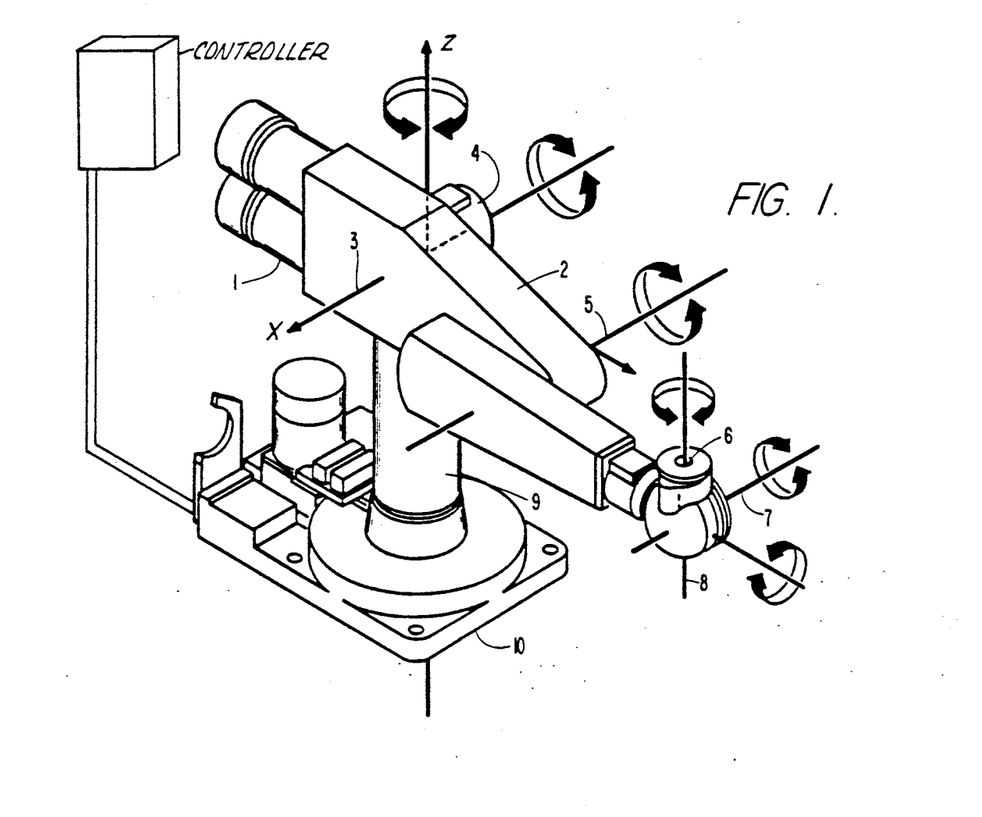
FIG. 1 is a plan view of a suitable robotic arm for use in practicing this invention.

One robotic arm suitable for use in an apparatus of this invention, and particularly useful in stereotactic neurosurgery—the Unimate PUMA Mark II 200 series robot system available from Unimation, Inc.—is illustrated in FIG. 1. This device 1 includes a mechanical arm 2 having six rotatable joints 3, 4, 5, 6, 7 and 8, each driven by a permanent magnet servomotor (not shown) through a gear train (also not shown). The mechanical arm 2 is supported so that the reference point is maintained e.g., on a pedestal 9 with associated mounting means 10. The direction and extent of rotation of each of the joints 3-8, inclusive, in relation to X, Y and Z axes are indicated in FIG. 1 by the circular arrows and degree indicia given at each joint (e.g., $-90°$, $0°$, $90°$, $+180°$ and $-180°$ around the Z axis at the joint 3). For the joints 3, 4 and 5, which provide waist, shoulder and elbow motions, respectively, the servomotors incorporate electromagnetic brakes that are activated whenever power is removed from the robotic arm. The joints 6, 7 and 8 provide wrist rotation, wrist bend and flange rotation, respectively, and an external clamp or stand (indicated by reference numeral 71 in FIG. 7) can be provided to support the end effector, i.e., joints 6, 7 and 8, of the robotic arm 1. All the servomotors used incorporate optical increment encoders (not shown) that provide position and velocity feedback to the robot's servosystem. The major hardware parameters for the Unimate PUMA Mark II 200 series robot system are summarized in Table 1 below:

TABLE I

| Robot Arm | |
|---|---|
| Axes | Six revolute axes |
| Clearance Required | Spherical volume with shoulder at center: 0.47 m (18.5 in.) radius to hand mount flange |
| Weight | 129 N (29 lb) |
| Drive | Electric DC servomotor |
| Maximum Inertia Load (Including Gripper) | Wrist rotation (J4) NOT exceed 1.0 in-oz-sec$^2$ Wrist Bend (J5) NOT exceed 1.8 in-oz-sec$^2$ Flange Rotation (J6) NOT exceed 0.5 in-oz-sec$^2$ |
| Position Repeatability | ±0.05 mm (±0 002 in) with primary work envelope |
| Tool Velocity | 1.0 m/s (3.3 fps) maximum (with maximum load within primary work envelope) |
| Software Movement Limits | |
| Waist - Joint 1 | −184 to 124 (308 degree) |
| Shoulder - Joint 2 | −247 to 67 (314 degree) |
| Elbow - Joint 3 | −56 to 236 (292 degree) |
| Wrist - Joint 4 | −223 to 355 (578 degree) |
| Wrist - Joint 5 | 122 to 122 (244 degree) |
| Wrist - Joint 6 | 222 to 312 (534 degree) |

Any other suitable remotely operable system or robotic means having the requisite degrees of freedom, for example, any robotic arm having the requisite number of joints to enable it to imitate the motions of the human arm and hand, i.e., ones having three or more joints such as the PUMA 560 and Stanford manipulators, can be employed in place of the Unimate PUMA Mark II Robot 200 series robotic arm in the novel apparatus of this invention.

Because of the need for great accuracy when performing many surgical techniques, an off-the-shelf robotic arm—particularly one having three or more joints, such as the aforementioned Unimate PUMA Mark II 200 series robotic arm, in which errors arising from less than perfect alignment of each joint (or perhaps better stated, less than perfect alignment or dimensioning of the gears, shims, etc. which make up each joint) will multiply as the number of joints present and the number of degrees of freedom resulting therefrom increases—may have to be calibrated (i.e., have its individual operating "signature" determined) before being incorporated into the novel apparatus of this invention to compensate for such errors and thus insure the requisite degree of accuracy.

One technique for calibrating the arm involves first driving the arm in a multiplicity of predetermined directions to randomly selected points in space within the arm's field of reach—with at least 28 directions or points being preferred for a 6 joint-containing arm; fewer directions or points being needed for arms having fewer joints—and having the arm fixedly engage, at each such point, a gauge block set in place to provide a precise, measured, immovable reference point at the location at which the arm engages the block. Next, the arm's joints are read (in the case of the aforementioned Unimate PUMA Mark II 200 series robotic arm by questioning the VAL or VAL II operating software which drives the arm) to give the difference between where the arm was told to go and where it actually went in each case. These differences, when fed into a Jacobian transform matrix (see the computer program below) provide the robot arm's "signature", compensate for any error arising from all the arm's joints by supplanting any positioning inaccuracies in the arm's positioning programming (e.g., VAL or VAL II operating software) and guarantee the requisite degree of accuracy in its subsequent positioning.

Other calibration techniques can be found in the literature; see, for example, Hayati et al, *J. Robotic Systs.*, 2 (4), 397–413 (1985).

Figure 2A:
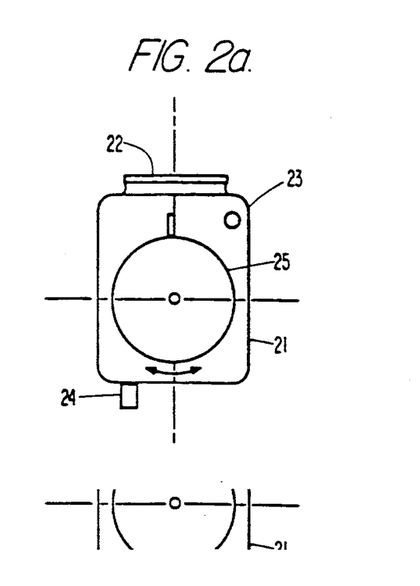
FIG. 2a comprise an end view and FIG. 2b a side view of a probe holder for attachment to the end effector of the robotic arm of FIG. 1, to permit the surgeon to guide a probe during a stereotactic procedure.
Figure 2B:
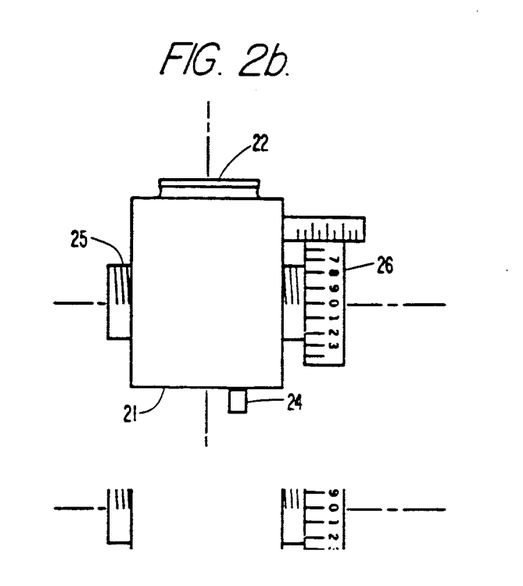

FIG. 2 shows a probe or surgical tool holder 21 which may be attached by suitable means (not shown) to the end effector of the robotic arm 1 shown in FIG. 1 (i.e., at the joint 6), so that the surgeon can guide the probe.

As shown in FIG. 2a, an end view of the probe holder 21, this holder includes a point of attachment 22 for affixing the probe holder 21 to the joint 6 of the robotic arm 1, hinge means 23 and quick release means 24, and sleeve or bushing means 25 having associated therewith a vernier fine adjustment scale 26 (shown in FIG. 2b, a side view of the probe holder 21). Such fine adjustments could also be controlled by a computer for which software to perform such adjustments can be designed in known manner.

The sleeve or bushing means 25 of the probe holder 21 makes fine tuning of the probe length possible. A quick release mechanism 24 allows the probe (see reference numeral 72 in FIG. 7) to be separated from the robotic arm 1. This feature is useful for multiple targets. It is also necessary for patients undergoing body stereotactic surgery because movement continues after the probe 72 is inserted.

An electronic controller (such as the one provided by the manufacturer with the Unimate PUMA Mark II Robot 200 series system) contains the built-in electronics for the robot system. The "brain" of the controller is a DEC LSI-11 minicomputer. Other computers could of course be adapted to this use. The Unimate PUMA Mark II 200 series robot's VAL or VAL II operating system software, also available from Unimation, Inc., supports the robot arm and both serial and parallel input/output peripheral devices such as a CRT terminal, a floppy disk, and a manual control unit. The controller also contains digital and analog circuits to control each joint of the robotic arm 1 as well as its power supply. A manual control unit allows a user to manipulate the robotic arm 1 in several modes through buttons and a speed control switch on the unit. When the panic button which is part of the manual control unit is pressed, all processes stop and every joint of the robotic arm 1 is frozen.

Since the LSI-11 microcomputer is designed for robot control only, it lacks the software needed for stereotactic computation programs. In addition, the robot system has to communicate with a CT scanner or like imaging means. Hence a host computer is used in conventional fashion to store the scanned images and run all the stereotactic software. A host Data General Eclipse or DEC 11/34 minicomputer, an IBM PC, combinations thereof, or any other such means for controlling the robotic arm 1 based at least in part upon information obtained from the imaging device, alone or together with other information, will communicate with the LSI-11 or other microcomputer via a standard RS-232C link or equivalent means. The surgeon interacts with the host computer, by means of a cursor on a computer screen controlled by a keyboard, a track ball, a joystick, a mouse, or the like, using stereotactic procedure computer software developed in known manner for this purpose. Such software developed for use with a host Data General Eclipse to interface a CT scanner an IBM PC, together with the IBM PC's software which drives the robotic arm 1, is attached hereto as Exhibit I. In this particular arrangement the Data General computer was connected to a GE imaging console having a joystick.

The computer program or software continuously monitors the angles or positions between all the joints of the robotic arm 1 in relation to each other joint, and controls the motion of each joint in relation to all the others. This permits the surgeon to precisely position the robot arm at any desired location in space relative to the body site being operated on.

Figure 3:
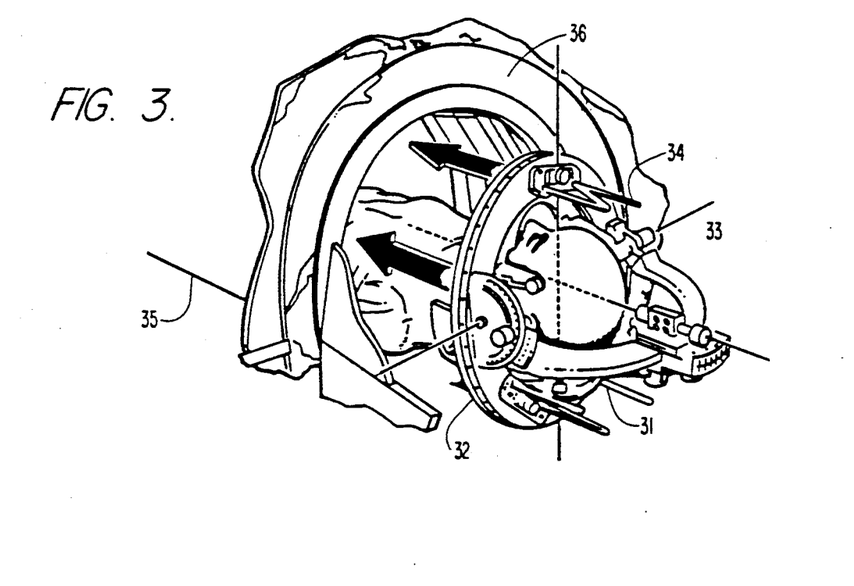
FIG. 3 is a plan view of a stereotactic head frame for use in practicing this invention.

FIG. 3 shows a stereotactic head frame 31 which can be used when practicing the novel method of this invention. The head frame 31 illustrated was adapted from a conventional stereotaxis frame by removing its arch. The ring structure 32, e.g., a metal ring, of the head frame 31 supports and fixes the patient's head with a head rest (not shown) and a suitable number, e.g., four, stainless steel-tipped screw pins, one of which is shown as a pin 33. A suitable number, e.g. three, of N-shaped locators, one of which is shown as a locator 34, to provide spatial position references mounted on the ring structure 32 can be used to determine the location of the scanned images, since they will show up in the cross-sectional images obtained by operating the CT scanner 36. The ring structure 32 in turn is attached to the sliding surface of a couch or carriage 35 which is part of the CT scanner 36.

Any other suitable means for fixing the head in place, such as webbing, Velcro straps, etc., can be used in place of the head frame 31.

After CT or other images are taken by the scanner 36, for convenience the patient can be translated or slid out of the scanner 36 to the work area of the robotic arm 1. Then the N-shaped locators 34 are removed and the robotic arm 1, the mechanical arm 2 of which is mounted on a pedestal 9, is attached to the ring structure 32 by its mounting means 10.

When using newer models of certain imaging devices, e.g., CT scanners, the patient can remain stationary within the device while the robotic arm 1 is being used. When using an MRI device, the patient can even be in a different room from that housing the main body of the imaging device.

Figure 4:
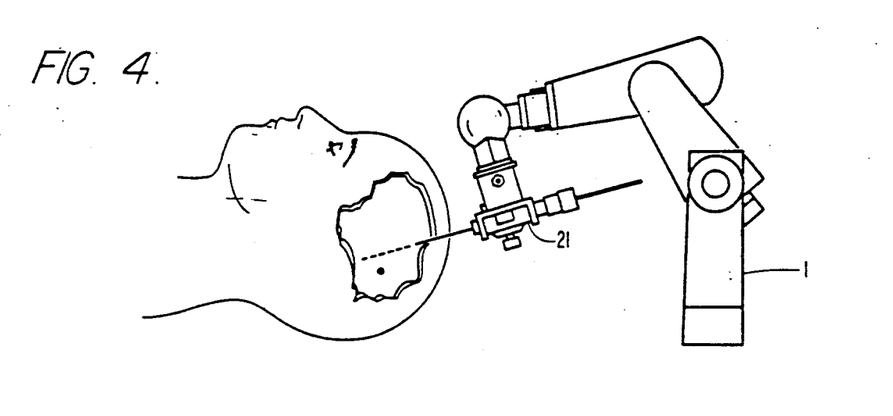
FIGS. 4-7, inclusive, are plan views of an apparatus of this invention as it would be positioned in use in stereotactic neurosurgery.

Next, the surgeon indicates a target point on one of the images provided by the CT or other imaging device. Using the trace of the N-shaped locators 34 in the image and the known position of the ring structure 32, the X-Y-Z coordinates of the target are transformed into the 3-D coordinate system of the robotic arm 1. The surgeon then maneuvers the robotic arm 1 to designate an appropriate entrance point on the skull. He also determines the approximate entry trajectory by directing the probe holder 21 (see FIG. 2), as shown in FIG. 4. Such maneuvers may be accomplished either by pushing buttons on the manual control unit of the robotic arm 1 or by setting the robotic arm 1 to the "free" mode and manually manipulating the robotic arm 1.

Figure 5:
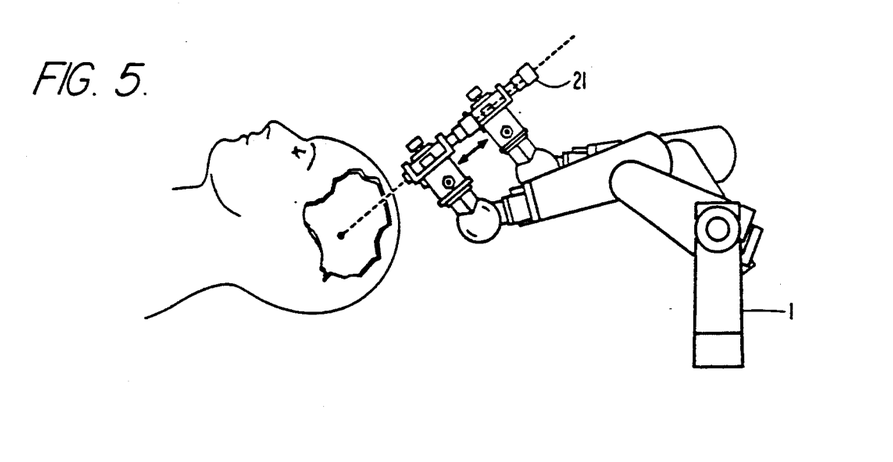
Figure 6:
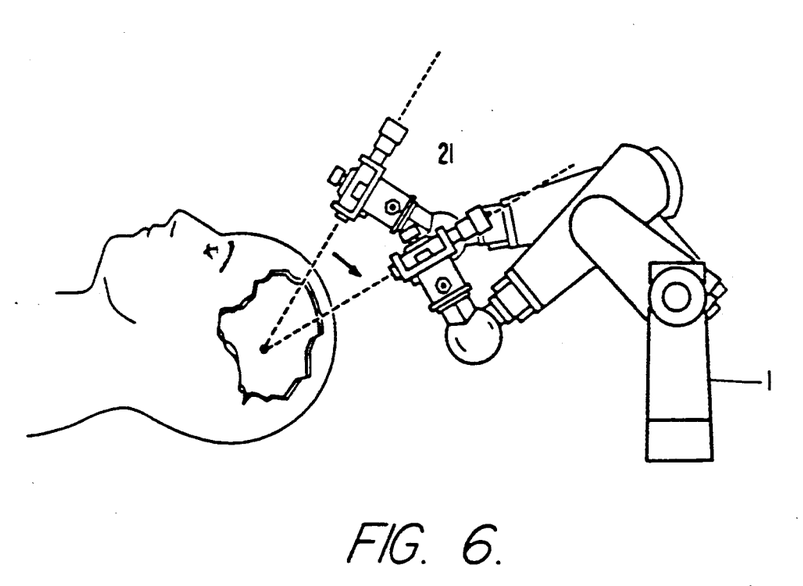

Stereotactic computer software designed in known fashion, e.g., the Data General and IBM PC software attached hereto as Exhibit I, is then used to activate the means for controlling the robotic arm 1, e.g., a host computer, to direct the robotic arm 1 to align the probe holder 21 with the trajectory determined by the entrance point and the target. Initially, the robotic arm 1 is driven in such a manner as to be a safe distance away from the head. By pushing two buttons on the manual controller, or by typing commands into a keyboard that interacts with the computer software, the surgeon may control the robotic arm 1 so that the probe holder 21 moves in or out along the trajectory, as shown in FIG. 5, as close to the head as desired. The surgeon can use the buttons on the manual control unit of the robotic arm 1 to alter the trajectory. The stereotactic computer software maintains the trajectory line of the probe holder 21 constantly pointing at the target, as shown in FIG. 6. Once the trajectory is determined, the bushing inside probe holder 21 is removed. A sterile bushing (not shown) is then inserted into the probe holder 21 and a sterile twist drill bit (not shown) is next inserted through the sterile bushing in order to drill a small burr hole (usually approximately ⅛ inch in diameter) in the skull. Thus, the surgeon can use the robotic arm 1 for a stable guide while boring a burr hole through the skull.

A robot vision system which will lock onto coordinates provided by a suitable locating means, e.g., an indelible marking, a removable ring having suitable locators, e.g., N-shaped locators such as that shown as the locator 34, a projected or stationary grid, or the like, can also be employed to guide the robotic arm 1.

Figure 7:
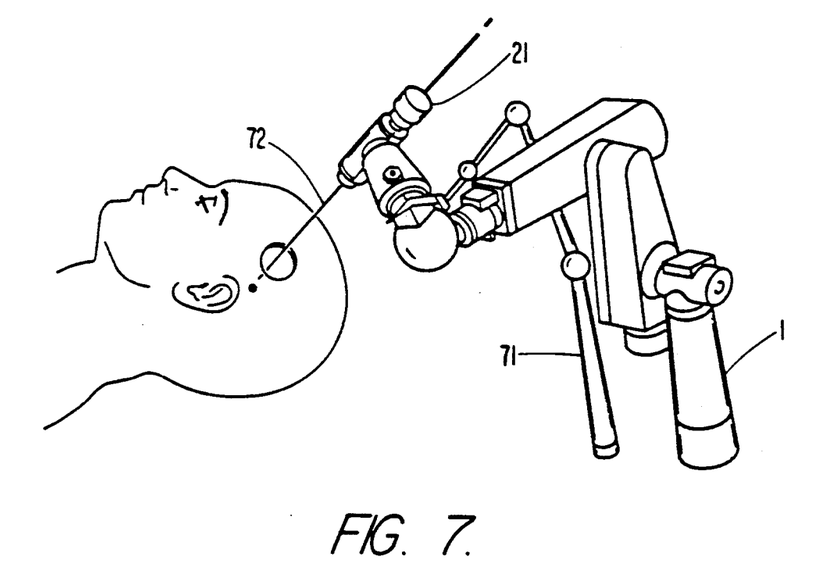

After the burr hole is drilled, the robotic arm 1 can be programmed by means of the stereotactic computer software to quickly retract to its standby position or, if desired, the robotic arm 1 can be left in place. As soon as the surgeon finishes cleaning and sterilizing the burr hole, the robotic arm 1 can be summoned back to the trajectory that it left. The probe holder 21 and the probe 72 are remounted on the robotic arm 1 and the surgeon is prepared for probe insertion. At this moment the surgeon can still modify the probe trajectory for slight adjustments. For example, a main artery might be avoided by a slight shift. The surgeon can fine-tune the final trajectory by pushing buttons on the manual control unit of the robotic arm 1 in a manner similar to the use of a joystick. The stereotactic software program maintains the probe direction, aiming at the target constantly.

Once the final trajectory is determined to the surgeon's satisfaction, he locks the robotic arm 1 by clamping its end effector with the external clamp or stand 71 as shown in FIG. 7. In this final configuration, the surgeon inserts the probe 72 manually. The threaded sleeve or bushing 25 on the probe holder 21, together with the vernier fine adjustment scale 26, or, as mentioned above, adjustment controlled by computer software, allows the surgeon to increase or decrease the computed probe length to whatever extent deemed necessary.

In cases such as hypothermia therapy, the surgeon may need to access many targets through different paths. Using the novel apparatus and method of this invention, the above procedure can easily be repeated as many times as necessary. Performing such procedure with a frame in the manner hitherto practiced in the art is impossibly tedious. Stereotactic software can direct the robotic arm 1 to access targets in parallel trajectories or any target and trajectory desired. After insertion, a quick release mechanism on the probe holder 21 permits the probe 72, or a catheter, cannula, needle or other surgical implements including neurosurgical and radio therapeutic implements such as endoscopic devices, lasers and implantation means for introducing radioactive isotopes into the body, to separate from the robotic arm 1 so the arm can move to another trajectory for reinsertion.

The robotic system of this invention has several important advantages over prior art frame-oriented systems. This novel robotic system is capable of fast, easy trajectory adjustments and is extremely flexible in its ability to allow for trajectory modifications. Such capability offers the surgeon a versatile tool which lends a helping hand while occupying a minimum of space. Sophisticated stereotactic operations can be performed by the surgical team with much less effort and time. Compared with the robotic stereotaxis system of this invention, typical prior art frame systems are primitive.

The robotic arm 1 eliminates human errors. The reading and setting of parameters in the stereotactic frame constitutes the major source of errors in a frame-oriented stereotaxis system. The robotic stereotaxis system of this invention does not require any human intervention, and hence eliminates the possibility for gross error originating from this source.

Robotic stereotaxis as taught herein can be applied to the head, the body and the limbs. No existing stereotactic frame can be applied satisfactorily to head, body and limb stereotaxis. Robotic stereotaxis has no fixed radius arch constraint, and thus eliminates drawbacks inherent in prior methods and apparatus, namely, a surgeon using prior apparatus cannot position the probe holder at an arbitrary distance from the patient and, in the case of prior art body frame systems, the arch is sensitive to an oversized patient.

When not in use, the robotic arm 1 easily removes itself completely from between the surgeon and the patient.

In addition to allowing wider access angles, the robotic arm 1, having as it does six degrees of freedom, offers an arbitrary trajectory at an arbitrary location within its working area, and thus has a much wider choice of accessing angles than a frame can be devised to provide and is capable of better accuracy. Though the precision provided by a stereotactic frame has often proved satisfactory, with angular precision of ±2 arc-seconds in a typical head frame setup, the robotic arm 1 can provide an even higher accuracy, since it is capable of placing probes to a Cartesian coordinate precision of ±0.05 mm. Such precision may be required in some delicate neurosurgery techniques.

Since the robotic arm 1 may reach a point of trajectory in many different ways, one must choose the preferred path required for safety and convenience. In other words, the stereotactic computer software employed should provide a smooth, predictable path that affords the least chance of striking the patient or another object. Although it is possible to enter environment contour information into the computer, this can be time consuming. However, by (a) letting the robotic arm 1 move at a speed sufficiently slow that a human can react in time, (b) allowing the computer program to move the robotic arm 1 only at a distance sufficiently far from the patient to avoid damage, and (c) keeping the manual control unit nearby, any positioning problems can be avoided. And, in an emergency a panic button installed as part of the control system can bring the robot system to a complete stop.

To date, computerized tomographic-aided robotic stereotaxis systems assembled in accordance with this invention have been employed in twenty different brain surgery procedures. One of them, for example, was a needle biopsy on a 52 year-old man with multiple brain tumors. The patient was conscious throughout the operation and left the hospital three days later. This system, when coupled with a 3-D display and a suitable radiation distribution pattern, can also permit a surgeon to perform internal radiation therapy quickly and efficiently.

The above discussion of this invention is directed primarily to preferred embodiments and practices thereof. It will be readily apparent to those skilled in the art that further changes and modifications in the actual implementation of the concepts described herein can readily be made without departing from the spirit and scope of the invention as defined by the following claims.

```
C This routine is used to get the Jacobian Transform for puma.
      SUBROUTINE JACOBIAN(TT, JCBN)
      IMPLICIT REAL*8 (A-H, O-Z)
      REAL*8 TT(6), JCBN(6, 6)
      A2 = 20.32
      A3 = 0.0
      D3 = 12.625
      D4 = 20.32
      DO 10, I = 1, 6
      DO 10, J = 1, 6
      JCBN(I, J) = 0.0
10    CONTINUE
      C1 = DCOS(TT(1))
      C2 = DCOS(TT(2))
      C3 = DCOS(TT(3))
      C4 = DCOS(TT(4))
      C5 = DCOS(TT(5))
      C6 = DCOS(TT(6))
      S1 = DSIN(TT(1))
      S2 = DSIN(TT(2))
      S3 = DSIN(TT(3))
      S4 = DSIN(TT(4))
      S5 = DSIN(TT(5))
      S6 = DSIN(TT(6))
      C4S6 = C4 * S6
      C4C6 = C4 * C6
      C4C5C6 = C4C6 * C5
      C4C5S6 = C4S6 * C5
      S4S5 = S4 * S5
      S4S6 = S4 * S6
      S4C6 = S4 * C6
      S4C5C6 = S4C6 * C5
      S4C5S6 = S4S6 * C5
      DUM1 = C4C5C6 - S4S6
      DUM2 = C4C5S6 + S4C6
      S5C6 = S5 * C6
      S5S6 = S5 * S6
      C4S5 = C4 * S5
      C23 = C2 * C3 - S2 * S3
      S23 = S2 * C3 + C2 * S3
      AA = D4 * S23 + A3 * C23 + A2 * C2
      DUMMY = DUM1 * C23 - S23 * S5C6
      JCBN(1, 1) = (S4C5C6 + C4S6) * AA - D3 * DUMMY
      DUMMY = DUM2 * C23 - S23 * S5S6
      JCBN(2, 1) = AA * (-S4C5S6 + C4C6) + D3 * DUMMY
      JCBN(3, 1) = -(C23 * C4S5 + S23 * C5) * D3 + AA * S4S5
      JCBN(4, 1) = -S23 * DUM1 - C23 * S5C6
      JCBN(5, 1) = S23 * DUM2 + C23 * S5S6
      JCBN(6, 1) = -S23 * C4S5 + C23 * C5
      JCBN(1, 2) = (D4 + A2 * S3) * DUM1 + (A2 * C3 + A3) * S5C6
      JCBN(2, 2) = -(A2 * C3 + A3) * S5S6 - (A2 * S3 + D4) * DUM2
      JCBN(3, 2) = (A2 * S3 + D4) * C4S5 - (A2 * C3 + A3) * C5
      JCBN(4, 2) = S4C5C6 + C4S6
      JCBN(5, 2) = -S4C5S6 + C4C6
      JCBN(6, 2) = S4S5
      JCBN(1, 3) = DUM1 * D4 + A3 * S5C6
      JCBN(2, 3) = -DUM2 * D4 - A3 * S5S6
      JCBN(3, 3) = -A3 * C5 + D4 * C4S5
      JCBN(4, 3) = JCBN(4, 2)
      JCBN(5, 3) = JCBN(5, 2)
      JCBN(6, 3) = S4S5
      JCBN(4, 4) = -S5C6
      JCBN(5, 4) = S5S6
      JCBN(6, 4) = C5
      JCBN(4, 5) = S6
      JCBN(5, 5) = C6
      JCBN(6, 6) = 1
      RETURN
      END
```

```
C
C This is the main program to control the robot arm to do brain
C surgery.
C The documentation of this program is specified in "The report
C of mathematic kenimatic approach of applying puma to brain surgery".
      IMPLICIT REAL*8 (A-H, O-Z)
      REAL*8 TB0(4,4),T06(4,4),T6E(4,4),TBH(4,4),TH(6),
     *  THC(6),TEMP(4,4),TBQ(4,4),TBF(4,4),COORD(4,4),TOOL(4,4),
     *  EMTX(2, 28),THOUT(6),TBOP(4, 4),TBT1(4, 4),TBT2(4, 4),
     *  TBT3(4, 4),TBT4(4, 4),TBT5(4,4 ),NDLEL,DETX,DETY,DETZ
      CHARACTER*6 A
      CHARACTER*1 AA
      CALL CLRSCRN
C Ask the mode user wants to use.
      WRITE(*, 1101)
1101  FORMAT(1X, '-> Enter 1 for normal operation, 2 for debugging: '\
     +)
      READ(*, *) MODE
      PI=3.141592
      DGTORD=PI/180.0
      RDTODG=180.0/PI
      H=34.2
C       Read errors in D.H. parameters from file 'EFILE.DAT' and store
C       in arra EMTX.
      CALL REFILE(EMTX, 2, 28)
10    IER = 1
      WRITE(*, 11)
11    FORMAT(1X,/,1X, '->Enter needle length in cm: '\)
      READ(*,*) NDLEL
      IF(NDLEL.LT.0) THEN
          WRITE(*,*) '-> Enter positive number, Try again !'
              GOTO 10
      ENDIF
C     Compute TB0 ( called TEMP) matrix without errors.
      DO 20 I=1,4
      DO 20 J=1,4
           TEMP(I,J)=0.0
20    CONTINUE
      TEMP(1,1)=1.0
      TEMP(2,2)=1.0
      TEMP(3,3)=1.0
      TEMP(4,4)=1.0
      TEMP(3,4)=H
C     Compute TB0 matrix, including D.H. parameters errors.
      TH0 = EMTX(1, 1) * DGTORD
      BT0 = EMTX(1, 2) * DGTORD
      D0  = EMTX(1, 3)
      AF0 = EMTX(1, 4) * DGTORD
      TBOP(1, 1) = DCOS(BT0)*DCOS(TH0)-DSIN(AF0)*DSIN(BT0)*DSIN(TH0)
      TBOP(1, 2) = -DCOS(AF0)*DSIN(TH0)
      TBOP(1, 3) = DSIN(BT0)*DCOS(TH0)+DSIN(AF0)*DCOS(BT0)*DSIN(TH0)
      TBOP(1, 4) = D0*DCOS(TH0)
      TBOP(2, 1) = DCOS(BT0)*DSIN(TH0)+DSIN(AF0)*DSIN(BT0)*DCOS(TH0)
      TBOP(2, 2) = DCOS(AF0)*DCOS(TH0)
      TBOP(2, 3) = DSIN(BT0)*DSIN(TH0)-DSIN(AF0)*DCOS(BT0)*DCOS(TH0)
      TBOP(2, 4) = D0*DSIN(TH0)
      TBOP(3, 1) = -DCOS(AF0)*DSIN(BT0)
      TBOP(3, 2) = DSIN(AF0)
      TBOP(3, 3) = DCOS(AF0)* DCOS(BT0)
      TBOP(3, 4) = 0.
      TBOP(4, 1) = 0.
      TBOP(4, 2) = 0.
      TBOP(4, 3) = 0.
      TBOP(4, 4) = 1.
      CALL MUL(TEMP, TBOP, TB0)
      IF (MODE .EQ. 2) CALL OUTM('TB0             ', TB0, 4, 4)
C     Compute T6E matrix without D.H. parameter errors.
      DO 30 I=1,4
      DO 30 J=1,4
           T6E(I,J)=0.0
30    CONTINUE
      T6E(1,1)=1.0
      T6E(2,3)=1.0
      T6E(2,4)=NDLEL
      T6E(3,2)=-1.0
      T6E(3,4)=9.15
      T6E(4,4)=1.0
C Ask user to enter information.
40    WRITE (*,41)
41    FORMAT(1X,/,1X,'Position the robot arm to the entry point.',
     +       /,1X, '->Enter six angle readings: '\)
      READ(*,*) (TH(I),I=1,6)
      WRITE(*,1000) (TH(I), I=1,6)
1000  FORMAT(1X, 'You entered: ',/,6F13.4)
      WRITE(*,43)
43    FORMAT(1X, '->Try again? [N]/Y '\)
```

```
                READ(*,'(A)')AA
                IF(AA.EQ.'Y'.OR. AA.EQ.'y' ) GOTO 40
50              CONTINUE
C               Add 2.78 degrees to TH(6)
                TH(6)=TH(6)+2.54
C Check the angles entered by user.
                IF((TH(1).LT.-180.0).OR.(TH(1).GT.120.0))THEN
                    WRITE(*,11000)'1'
11000           FORMAT(1H ,'*** Joint ',A1,' out of range, Try again ! ***')
                    GOTO 10
                ENDIF
                IF(((TH(2).GT.67).AND. (TH(2).LT.110)).OR.(TH(2).LT.-180))THEN
                    WRITE(*,11000) '2'
                    GOTO 10
                ENDIF
                IF((TH(3).LT.-56).AND. (TH(3).GT.-124).OR.(TH(3).GT.180.0))THEN
                    WRITE(*,11000)'3'
                    GO TO 10
                ENDIF
                IF((TH(4).LT.-222.0).OR.(TH(4).GT.354.))THEN
                    WRITE(*,110000)'4'
                    GO TO 10
                ENDIF
                IF((TH(5).LT.-121.0).OR.(TH(5).GT.121.0))THEN
                    WRITE(*,11000)'5'
                    GO TO 10
                ENDIF
                IF((TH(6).LT.-221.0).OR.(TH(6).GT.311.))THEN
                    WRITE(*,11000)'6'
                    GO TO 10
                ENDIF
52              WRITE(*,51)
51              FORMAT(1X,/,1X,'Specify configurations of shoulder and elbow.',
     +          /, 1X, '1 for right shoulder, -1 for left; 1 for elbow up, -1 for
     +          down.',/, 1X, '->Enter your selection (Shoulder, Elbow): '\)
                READ(*, *) IR,IUP
                WRITE(*, 53)  IR, IUP
53              FORMAT(1X, 'You enter: ', I2, ', ', I2)
                WRITE(*, 43)
                READ(*, '(A)') AA
                IF ((AA .EQ. 'Y') .OR. (AA .EQ. 'y')) GOTO 52
C Transfer theata from degrees to radians
                DO 2 I=1,6
2                   TH(I)=TH(I)*DGTORD
C Compute T06)
                CALL FORKIN(TH,T06)
C Compute TBH=TB0*T06*T6E
                CALL MUL(TB0,T06,TEMP)
                CALL MUL(TEMP,T6E,TBH)
                IF (MODE .EQ. 2) CALL OUTM('TBH            ',TBH,4,4)
C Compute a new TBH such that its Z-axis will point to target.
C Call this new frame Q. Thus compute TBQ.
                TBQ(1,4)=TBH(1,4)
                TBQ(2,4)=TBH(2,4)
                TBQ(3,4)=TBH(3,4)
C Ask informations from user.
60              WRITE(*,61)
61              FORMAT(1X,/,1X, '->Enter target X,Y, Z coordinates in cm: '\)
                READ(*,*)TX,TY,TZ
                WRITE(*,1200)  TX,TY,TZ
1200            FORMAT(1X 'You entered: TX ',F10.5,'  TY= ',F10.5,
     *          '  TZ= ',F10.5,/,1X, '->Try again? [N]/Y'\)
                READ(*,'(A)')AA
                IF(AA.EQ.'Y'.OR.AA.EQ.'y') GOTO 60
                T1=TX-TBQ(1,4)
                T2=TY-TBQ(2,4)
                T3=TZ-TBQ(3,4)
                AROOT=SQRT(T12+T22+T3**2)
                IF(ABS  (AROOT) .LT. 1.0) THEN
                    WRITE(*,*)'*** Target is the same as the entry point! ***'
                    WRITE(*,43)
                    READ (*, '(A)') AA
                    IF ((AA .EQ. 'Y') .OR. (AA .EQ. 'y')) GOTO 10
                    STOP
                ENDIF
C Find the entry point to target direction cosine.
                TBQ(1,3)=(TX-TBQ(1,4))/AROOT
                TBQ(2,3)=(TY-TBQ(2,4))/AROOT
                TBQ(3,3)=(TZ-TBQ(3,4))/AROOT
C       Obtain the X and Y axies of TBQ.
                TBQ(1,1)=-TBH(3,2)*TBQ(2,3)+TBH(2,2)*TBQ(3,3)
                TBQ(2,1)= TBH(3,2)*TBQ(1,3)-TBH(1,2)*TBQ(3,3)
                TBQ(3,1)=-TBH(2,2)*TBQ(1,3)+TBH(1,2)*TB1(2,3)
                TL1=SQRT(TBQ(1,1)**2+TBQ(2,1)**2+TBQ(3,1)**2)
                TBQ(1,1)= TBQ(1,1)/TL1
                TBQ(2,1)= TBQ(2,1)/TL1
                TBQ(3,1)= TBQ(3,1)/TL1
```

```
              TBQ(1,2)=-TBQ(3,3)*TBQ(2,1)+TBQ(2,3)*TBQ(3,1)
              TBQ(2,2)= TBQ(3,3)*TBQ(1,1)-TBQ(1,3)*TBQ(3,1)
              TBQ(3,2)=-TBQ(2,3)*TBQ(1,1)+TBQ(1,3)*TBQ(2,1)
              TL2=SQRT(TBQ(1,2)**2+TBQ(2,2)**2+TBQ(3,2)**2)
              TBQ(1,2) = TBQ(1,2)/TL2
              TBQ(2,2) = TBQ(2,2)/TL2
              TBQ(3,2) = TBQ(3,2)/TL2
              TBQ(4,1)=0.0
              TBQ(4,2)=0.0
              TBQ(4,3)=0.0
              TBQ(4,4)=1.0
              IF (MODE .EQ. 2) CALL OUTM('TBQ             ',TBQ,4,4)
C Ask user to enter information.
65            WRITE(*,123)
123           FORMAT(/,1X,'->Enter the distance in cm that the end-effector',
             + /,1X ,'must be positioned from the entry point: '\)
70            READ(*,*) Z
              WRITE(*,71)Z
71            FORMAT(1X, 'You enter: ', F10.4)
              WRITE(*, 43)
              READ(*, '(A)') AA
              IF ((AA .EQ. 'y') .OR. (AA .EQ. 'Y')) GOTO 65
              IF(Z .LT. 0.0) THEN
                  WRITE(*,*)'*** Enter positive number ! ***'
                  GOTO 65
              ENDIF
              OLDZ = Z
C             Compute the goal position for the robot end-effector.
              CALL UNITM(TEMP)
              TEMP(3,4)=-Z
              CALL MUL(TBQ,TEMP,TBF)
              IF (MODE .EQ. 2) CALL OUTM('TBF             ',TBF,4,4)
              Z=Z+AROOT
C             Compute the new T6E.  Set needle length to 0.
              T6E(2,4)=0.0
C             Form COORD coordinate.
              CALL INVM(TB0,COORD)
C             Get T06
              CALL INVM(T6E,TOOL)
              CALL MUL(COORD, TBF, TEMP)
              CALL MUL(TEMP, TOOL, T06)
C             Get result theata including D.H. parameter errors
              CALL JCERROR(T06, IR, IUP, TH, EMTX, MODE, IER)
              IF (IER .NE. 1) THEN
                  WRITE(*,43)
                  READ(*, '(A)') AA
                  IF ((AA .EQ. 'Y') .OR. (AA .EQ. 'y')) GOTO 10
                  STOP
              ENDIF
              TH(6)=TH(6)-2.54*DGTORD
              DO 99 ,I = 1, 6
              TH(I) = TH(I) * RDTODG
              THOUT(I) = TH(I)
99            CONTINUE
C Output the result on screen
101           CALL CLRSCRN
              IF (IER .NE. 1) THEN
                  WRITE(*, *) 'Note: last attempt is failed, the following data is
             + old one.'
                  IER = 1
              ENDIF
              WRITE(*, *) '                     ------------------- PARAMETER -----
             +----------------'
              WRITE(*, *)
              WRITE(*, 302) TX, TY, TZ
302           FORMAT(1X, 'Target(X, Y, Z): ', 3F10.4)
              WRITE(*, 303) IR, IUP
303           FORMAT(1X, 'Configuration(shoulder, elbow): ', I2,' , ', I2)
              WRITE(*, 304) OLDZ
304           FORMAT(1X, 'Length from end-effector to head: ', F10.4)
              WRITE(*, *) '                     ------------------- RESULT --------
             +----------------'
              WRITE(*, *)
              CALL OUTV('TH1-T06         ',THOUT,6)
              DO 98 ,I = 1, 6
              TH(I) = TH(I) * DGTORD
98            CONTINUE
              WRITE(*,1300) Z
1300          FORMAT(1X,'Needle length: ',F10.3)
              WRITE (*,*)
              WRITE (*,*)
              WRITE (*,*)'                     -------------------- MENU ---------
             +----------------'
              WRITE(*,*)
              WRITE(*,*) '1) To change the target by small amount. '
              WRITE(*,*) '2) To move the trajectory path in parallel.
              WRITE(*,*) '3) To change the distance between the head and th
```

```
              +e end-effector.'
              WRITE(*,*) ' 4) To start from the beginning.'
              WRITE(*,*) ' 5) To stop.'
              WRITE(*, 102)
102           FORMAT(1X,/, 20X, 'Selection: '\)
              READ (*,*) IGOTO
              CALL CLRSCRN
              CALL EQU(TBQ, TBT1)
              CALL EQU(TBF, TBT2)
              CALL EQU(T6E, TBT3)
              CALL EQU(T06, TBT4)
              CALL EQU(TBH, TBT5)
              PTX = TX
              PTY = TY
              PTZ = TZ
              PZ = Z
              POLDZ = OLDZ
              GOTO(91,92,93,94,95) IGOTO
C This is the first choice of the menu
91            WRITE (*,*) 'Selection #1'
              WRITE (*,504)
504           FORMAT(1X, '->Enter the amount of changes to X Y Z: '\)
              READ (*,*) DETX,DETY,DETZ
              WRITE (*,1000) DETX,DETY,DETZ
              WRITE (*,503)
503           FORMAT(1X, '->Try again? (Y/[N]) '\)
              READ (*,'(A)') AA
              IF (AA .EQ. 'Y' .OR. AA .EQ. 'y' ) GOTO 91
              TX = TX + DETX
              TY = TY + DETY
              TZ = TZ + DETZ
              T1=TX-TBQ(1,4)
              T2=TY-TBQ(2,4)
              T3=TZ-TBQ(3,4)
              AROOT=SQRT(T12+T22+T3**2)
              IF(ABS (AROOT) .LT. 1.0) THEN
              WRITE(*,*) '*** Target is the same as the entry point! ***'
              IER = 0
              GOTO 601
              ENDIF
C Find the entry point to target direction cosine.
              TBQ(1,3) =(TX-TBQ(1,4))/AROOT
              TBQ(2,3) =(TY-TBQ(2,4))/AROOT
              TBQ(3,3) =(TZ-TBQ(3,4))/AROOT
C Obtain the X and Y axies of TBQ.
              TBQ(1,1)=-TBH(3,2)*TBQ(2,3)+TBH(2,2)*TBQ(3,3)
              TBQ(2,1)= TBH(3,2)*TBQ(1,3)-TBH(1,2)*TBQ(3,3)
              TBQ(3,1)=-TBH(2,2)*TBQ(1,3)+TBH(1,2)*TBQ(2,3)
              TL1=SQRT(TBQ(1,1)**2+TBQ(2,1)**2+TBQ(3,1)**2)
              TBQ(1,1) = TBQ(1,1)/TL1
              TBQ(2,1) = TBQ(2,1)/TL1
              TBQ(3,1) = TBQ(3,1)/TL1
              TBQ(1,2)=-TBQ(3,3)*TBQ(2,1)+TBQ(2,3)*TBQ(3,1)
              TBQ(2,2)= TBQ(3,3)*TBQ(1,1)-TBQ(1,3)*TBQ(3,1)
              TBQ(3,2)=-TBQ(2,3)*TBQ(1,1)+TBQ(1,3)*TBQ(2,1)
              TL2=SQRT(TBQ(1,2)**2+TBQ(2,2)**2+TBQ(3,2)**2)
              TBQ(1,2) = TBQ(1,2)/TL2
              TBQ(2,2) = TBQ(2,2)/TL2
              TBQ(3,2) = TBQ(3,2)/TL2
              TBQ(4,1)=0.0
              TBQ(4,2)=0.0
              TBQ(4,3)=0.0
              TBQ(4,4)=1.0
              IF (MODE .EQ. 2) CALL OUTM('TBQ              ',TBQ,4,4)
C Compute the goal position for the robot end-effector by old Z.
              CALL UNITM (TEMP)
              TEMP(3,4) = -OLDZ
              CALL MUL(TBQ,TEMP,TBF)
              IF (MODE .EQ. 2) CALL OUTM('TBF              ',TBF,4,4)
              Z = OLDZ + AROOT
C             Compute the new T6E.  Set needle length to 0.
              T6E(2,4)=0.0
C             Form COORD coordinate.
              CALL INVM(TB0,COORD)
C             Get T06
              CALL INVM(T6E, TOOL)
              CALL MUL(COORD, TBF, TEMP)
              CALF MUL(TEMP, TOOL, T06)
C             Get theata including parameter errors.
              CALL JCERROR (T06, IR, IUP, TH, EMTX, MODE IER)
C Recover from failed attempt.
601           IF(IER .NE. 1) THEN
              WRITE(*, *) 'Hit return to continue.'
              READ(*, '(A)') AA
```

```
              CALL EQU(TBT1, TBQ)
              CALL EQU(TBT2, TBF)
              CALL EQU(TBT3, T6E)
              CALL EQU(TBT4, T06)
              CALL EQU(TBT5, TBH)
              TX = PTX
              TY = PTY
              TZ = PTZ
              Z = PZ
              OLDZ = POLDZ
              GOTO 101
              ENDIF
              TH(6)=TH(6)-2.54*DGTORD
              DO 219, I= 1, 6
              TH(I) = TH(I) * RDTODG
              THOUT(I) = TH(I)
219           CONTINUE
              GOTO 101
C This is the second choice of the menu.
92            WRITE (*,*) 'Selection #2'
              WRITE (*,505)
505           FORMAT(1X, '->Enter the amount of parallel changes to X Y Z :'\)
              READ (*,*) DETX,DETY,DETZ
              WRITE (*,1000) DETX,DETY,DETZ
              WRITE (*,503)
              READ (*,'(A)') AA
              IF (AA .EQ. 'Y' .OR. AA .EG. 'y' ) GOTO 92
              TBH(1,4) = TBH(1,4) + DETX
              TBH(2,4) = TBH(2,4) + DETY
              TBH(3,4) = TBH(3,4) + DETZ
              TX = TX + DETX
              TY = TY + DETY
              TZ = TZ + DETZ
              TBQ(1,4) = TBH(1,4)
              TBQ(2,4) = TBH(2,4)
              TBQ(3,4) = TBH(3,4)
              T1 = TX - TBQ(1,4)
              T2 = TY - TBQ(2,4)
              T3 = TZ - TBQ(3,4)
              AROOT=SQRT(T1**2+T2**2+T3**2)
              IF(ABS (AROOT) .LT. 1.0) THEN
              WRITE(*,*)'*** Target is the same as the entry point ! ***'
              IER = 0
              GOTO 603
              ENDIF
C Find the entry point to target direction cosine.
              TBQ(1,3) =(TX-TBQ(1,4))/AROOT
              TBQ(2,3) =(TY-TBQ(2,4))/AROOT
              TBQ(3,3)=(TZ-TBQ(3,4))/AROOT
C Obtain the X and Y axies of TBQ.
              TBQ(1,1)=-TBH(3,2)*TBQ(2,3)+TBH(2,2)*TBQ(3,3)
              TBQ(2,1)= TBH(3,2)*TBQ(1,3)-TBH(1,2)*TBQ(3,3)
              TBQ(3,1)=-TBH(2,2)*TBQ(1,3)+TBH(1,2)*TBQ(2,3)
              TL1=SQRT(TBQ(1,1)**2+TBQ(2,1)**2+TBQ(3,1)**2)
              TBQ(1,1) = TBQ(1,1)/TL1
              TBQ(2,1) = TBQ(2,1)/TL1
              TBQ(3,1) = TBQ(3,1)/TL1
              TBQ(1,2)=-TBQ(3,3)*TBQ(2,1)+TBQ(2,3)*TBQ(3,1)
              TBQ(2,2)= TBQ(3,3)*TBQ(1,1)-TBQ(1,3)*TBQ(3,1)
              TBQ(3,2)=-TBQ(2,3)*TBQ(1,1)+TBQ(1,3)*TBQ(2,1)
              TL2=SQRT(TBQ(1,2)**2+TBQ(2,2)**2+TBQ(3,2)**2)
              TBQ(1,2) = TBQ(1,2)/TL2
              TBQ(2,2) = TBQ(2,2)/TL2
              TBQ(3,2) = TBQ(3,2)/TL2
              TBQ(4,1)=0.0
              TBQ(4,2)=0.0
              TBQ(4,3)=0.0
              TBQ(4,4)=1.0
              IF(MODE .EQ. 2) CALL OUTM('TBQ              ',TBQ,4,4)
C             Compute the goal position for the robot end-effector by Z.
              CALL UNITM(TEMP)
              TEMP(3,4) = -OLDZ
              CALL MUL (TBQ,TEMP,TBF)
              IF (MODE .EQ. 2) CALL OUTM('TBF              ',TBF,4,4)
              Z = OLDZ + AROOT
C             Compute the new T6E.  Set needle length to 0.
              T6E(2,4)=0.0
C             Form COORD coordinate.
              CALL INVM(TB0,COORD)
C             Get T06
              CALL INVM(T6E, TOOL)
              CALL MUL(COORD, TBF, TEMP)
              CALL MUL(TEMP, TOOL, T06)
C             Get theata including parameter erroes.
              CALL JCERRO(T06, IR, IUP, TH, EMTX, MODE, IER)
603           IF(IER .NE. 1) THEN
              WRITE (*, *) 'Hit return to continue.'
```

```
              READ(*, '(A)') AA
              CALL EQU(TBT1, TBQ)
              CALL EQU(TBT2, TBF)
              CALL EQU(TBT3, T6E)
              CALL EQU(TBT4, T06)
              CALL EQU(TBT5, TBH)
              TX = PTX
              TY = PTY
              TZ = PTZ
              Z = PZ
              OLDZ = POLDZ
              GOTO 101
              ENDIF
              TH(6)=TH(6)-2.54*DGTORD
              DO 229, I= 1, 6
              TH(I) = TH(I) * RDTODG
              THOUT(I) = TH(I)
229           CONTINUE
              GOTO 101
C This is the third choice of the menu.
93            WRITE (*,8) 'Selection # 3'
              WRITE (*,506)
506           FORMAT(1X, '->Enter the value you want to change: '\)
              READ (*,*) OLDZ
              WRITE(*, 1000) OLDZ
              WRITE(*, 503)
              READ (*, '(A)') AA
              IF ((AA .EQ. 'Y') .OR. (AA .EQ. 'y')) GOTO 93
                  WRITE(*,*) '*** Enter positive number ! *** '
                  GOTO 93
              ENDIF
C Compute the goal position for the robot end-effector by Z.
              DO 63 I = 1,4
              DO 63 J = 1,4
                  TEMP(I,J) = 0.0
63            CONTINUE
              TEMP(1,1) = 1.0
              TEMP(2,2) = 1.0
              TEMP(3,3) = 1.0
              TEMP(4,4) = 1.0
              TEMP(3,4) = -OLDZ
              CALL MUL (TBQ,TEMP,TBF)
              IF (MODE .EQ. 2) CALL OUTM('TBF',TBF,4,4)
              Z = OLDZ + AROOT
C Compute the new T6E.  Set needle length to 0.
              T6E(2,4)=0.0
C Form COORD coordinate.
              CALL INVM(TB0,COORD)
C             Get T06
              CALL INVM(T6E, TOOL)
              CALL MUL(COORD, TBF, TEMP)
              CALL MUL(TEMP, TOOL, T06)
C Get theata including parameter errors.
              CALL JCERROR(T06, IR, IUP, TH, EMTX, MODE, IER)
              IF (IER .NE. 1) THEN
              CALL EQU(TBT1, TBQ)
              CALL EQU(TBT2, TBF)
              CALL EQU(TBT3, T6E)
              CALL EQU(TBT4, T06)
              CALL EQU(TBT5, TBH)
              TX = PTX
              TY = PTY
              TZ = PTZ
              Z = PZ
              OLDZ = POLDZ
              GOTO 101
              ENDIF
              TH(6)=TH(6)-2.54*DGTORD
              DO 239, I= 1, 6
              TH(I) = TH(I) * RDTODG
              THOUT(I) = TH(I)
239           CONTINUE
              GOTO 101
C This is the fourth choice of the menu.
94            WRITE (*,508)
508           FORMAT(1X, '->Are you sure ? (Y/[N] '\)
              READ (*,'(A)') AA
              IF (AA .EQ. 'Y' .OR. AA .EQ. 'y') GOTO 10
              GOTO 101
C This is the fifth choice of the menu.
95            WRITE (*,509)
509           FORMAT(1X, '-> Are you sure ? (Y/[N])'\)
              READ (*,'(A)') AA
              IF (AA .EQ. 'Y' .OR. AA .EQ. 'y' ) GOTO 96
              GOTO 101
96            STOP
              END
```

I claim:

1. An apparatus for conducting stereotactic surgery comprising:
   (1) an imaging device for generating information regarding the structure of the bodily location to be operated on;
   (2) a robotic arm having rotatable joints, and
   (3) means for controlling the robotic arm based at least in part upon information received from the imaging device.

2. An apparatus as recited in claim 1 wherein the imaging device is a computerized tomography axial imaging system.

3. An apparatus as recited in claim 1 wherein the imaging device is a magnetic resonance imaging device.

4. An apparatus as recited in claim 1 wherein the imaging device is an ultrasound device.

5. An apparatus as recited in claim 1 wherein the imaging device is a mammograph machine.

6. An apparatus as recited in claim 1 wherein a combination of two imaging devices is employed.

7. An apparatus as recited in claim 6 wherein said imaging devices are a computerized axial tomography imaging system and a magnetic resonance imaging device.

8. An apparatus as recited in claim 1 wherein the robotic arm has an effector end to which there is affixed a probe holder.

9. An apparatus as recited in claim 8 wherein the probe holder holds a surgical implement.

10. An apparatus as recited in claim 9 wherein the surgical implement is a surgical probe.

11. An apparatus as recited in claim 9 wherein the surgical implement is a catheter.

12. An apparatus as recited in claim 1 wherein the means for controlling the robotic arm is a computer.

13. A method for conducting stereotactic surgery comprising:
    (1) generating information regarding the structure of the bodily location to be operated on using an imaging device;
    (2) supplying the information generated by the imaging device to a means for controlling a robotic arm,
    (3) manipulating the robotic arm by the controlling means in a manner based at least in part upon the information supplied to the controlling means by the imaging device.

14. A method as recited in claim 13 wherein the means for controlling the robotic arm has been calibrated by:
    (a) initially driving the robotic arm in a multiplicity of predetermined directions to randomly selected points in space within the robotic arm's field of reach;
    (b) having the robotic arm fixedly engage, at each such point in space, a means set in place at said point to provide a precise, measured, immovable reference point at the location at which the robotic arm engages said means;
    (c) reading the robotic arm's rotatable joints at each such point in space to give the difference between where the robotic arm was directed to go and where it actually went, and
    (d) feeding these differences into a Jacobian transform matrix to supplement any positioning inaccuracies in the controlling means' initial positioning of the robotic arm.

* * * * *